United States Patent [19]

Delumeau et al.

[11] Patent Number: 5,686,475
[45] Date of Patent: Nov. 11, 1997

[54] APPLICATION OF RILUZOLE IN THE TREATMENT OF MITOCHONDRIAL DISEASES

[75] Inventors: Jean-Christophe Delumeau, Antony; Michel Martinet, Paris; Michel Reibaud, Creteil; Jean-Marie Stutzmann, Villecresnes, all of France

[73] Assignee: Rhone-Poulenc Rorer S.A., Antony, France

[21] Appl. No.: 669,530

[22] PCT Filed: Jan. 9, 1995

[86] PCT No.: PCT/FR95/00023

§ 371 Date: Jul. 11, 1996

§ 102(e) Date: Jul. 11, 1996

[87] PCT Pub. No.: WO95/19170

PCT Pub. Date: Jul. 20, 1995

[30] Foreign Application Priority Data

Jan. 12, 1994 [FR] France .................... 94 00249

[51] Int. Cl.⁶ .................................................. A61K 31/425
[52] U.S. Cl. ............................................................ 514/367
[58] Field of Search .................................................. 524/367

[56] References Cited

U.S. PATENT DOCUMENTS 5,236,940  8/1993  Audiau et al. ........................ 514/164

FOREIGN PATENT DOCUMENTS

| 0 282 971 | 9/1988 | European Pat. Off. . |
| 0 374 041 | 6/1990 | European Pat. Off. . |
| 0 558 861 | 9/1993 | European Pat. Off. . |
| WO 94/05275 | 3/1994 | WIPO . |
| WO 94/06428 | 3/1994 | WIPO . |

OTHER PUBLICATIONS

Meldrum, B.S., "Anti–excitatory amino acid approach in the treatmetn of neurodengenerative disorders," Eur. Neuropsychopharmacol. (Netherlands), vol. 3, No. 3, (1993), pp. 184–185.

Martin, D., et al., "The neuroprotective agent riluzole inhibits release of glutamate and aspartate from slices of hippocampal area CA1," Eur. J. Pharmacol., vol. 250, No. 3, (1993), pp. 473–476.

Nonaka, I., "Mitochondrial diseases," Current Opinion in Neurology and Neurosurgery, vol. 5, No. 5, (1992), pp. 622–632.

Matthews, P.M., "Proton MR spectroscopic characterization of differences in regional brain metabolic abnormalities in mitochondrial encephalomyopathies," Neurology, vol. 43, No. 12, (1993), pp. 2484–2490.

*Primary Examiner*—Phyllis G. Spivack
*Attorney, Agent, or Firm*—Finnegan, Henderson, Farabow, Garrett & Dunner, L.L.P.

[57] ABSTRACT

A method for the treatment of mitochondrial diseases, including Kearns-Sayre syndrome, MERRF syndrome, MELAS syndrome and Leber's disease, is carried out by administering to a patient in need of treatment an effective amount of riluzole or a pharmaceutically acceptable salt thereof.

4 Claims, No Drawings

APPLICATION OF RILUZOLE IN THE TREATMENT OF MITOCHONDRIAL DISEASES

This application is a 371 of PCT/FR95/00023 Jan. 9, 1995.

The present invention relates to a novel therapeutic application of riluzole or the pharmaceutically acceptable salts of this compound.

Riluzole, or 2-amino-6-trifluoromethoxybenzothiazole, is useful as an anticonvulsant, anxiolytic and hypnotic medicinal product (EP Patent 50 551), in the treatment of schizophrenia (EP 305 276), in the treatment of sleep disorders and depression (EP 305 277), in the treatment of cerebrovascular disorders and as an anaesthetic (EP 282 971).

It has now been found, surprisingly, that this compound may also be used in the treatment of mitochondrial diseases.

Mitochondrial diseases are degenerative diseases which are linked to different mechanisms such as, for example, anomalies of mitochondrial DNA (deletions, point mutations, depletions, duplications), anomalies of cellular DNA coding for mitichondrial enzymes or complex macromolecular mitochondrial elements, acquired conditions caused by toxic substances (for example MPTP or CO) or by medicinal products (for example chloramphenicol, AZT or acetylsalicylic acid). Mitochondrial diseases which may be mentioned are Kearns-Sayre syndrome, MERRF syndrome (Myoclonic Epilepsy with Ragged Red Fibres), MELAS syndrome (Mitochondrial Encephalopathy, Myopathy, Lactic Acidosis and Stroke-like episodes) and Leber's disease (I. Nonaka, Current Opinion in Neurology and Neurosurgery, 5 (1992) 622).

The action of riluzole in the treatment of mitochondrial diseases is demonstrated by its protective effect in the cyanide test. It is known in fact that potassium cyanide exerts a toxic effect by inhibition of cytochrome oxidase aa3, the terminal enzyme in the electron transport sequence at the mitochondrial level. Thus in mice potassium cyanide (3 mg/kg i.v.) induces abdominal contractions and tonic attacks followed by death within 20 seconds.

Male adult mice weighing 22–25 g (CD1 COBS, Charles River), housed under controlled temperature and lighting conditions, receive food and drinking water ad libitum. The vehicle or the product to be studied is given to groups of 6 animals, either intraperitoneally 30 minutes before the intravenous bolus administration of a lethal dose (3 mg/kg) of potassium cyanide, or orally 1 hour before the administration of potassium cyanide. In the control group, all of the mice die within 20 seconds, whereas the ED50 for riluzole i.p. is 4.5 mg/kg and the ED50 for riluzole p.o. is 7.8 mg/kg.

The action of riluzole in the treatment of mitochondrial diseases is also demonstrated by its effect on the mitochondrial metabolism of the rat liver.

The metabolic activity of the mitochondrion is monitored by the consumption of oxygen by polarography, using a Clark electrode (marketed by Bioblock). The experimental setup consists of a glass chamber thermostated at 27° C. by a hot water system. A magnetic bar placed within the chamber permits continuous stirring of the reaction medium and facilitates the establishment of equilibrium between the dissolved oxygen and the gas diffusing through the membrane of the electrode. The mitochondria, the substrate (succinate) and ADP (adenosine diphosphate) are introduced into the reaction chamber through a small aperture situated in the upper part of the apparatus. A Clark electrode is immersed in the reaction medium via an opening which is hermetically sealed by a screw stopper. The consumption of oxygen is plotted by a recorder which is connected to a YSI model 5300 Biological Oxygen Monitor (marketed by Bioblock).

Mitochondria from the liver of the male SD rat are isolated at +4° C. by differential centrifugation according to the method described by Appelmans et al., Biochem. J., 59 (1955) 438–445. The mitochondrial pellet is taken up in from 1 to 3 ml of 0.25M sucrose buffer and homogenized using a pipette.

The oxygen consumption of the mitochondria (1.2 mg of proteins per ml) is measured in 5 ml of Chance buffer, consisting of 12 mM of NaF, 26 mM of NaCl, 58 mM of KCl and 3 mM of succinate substrate, so as to bring about the metabolic state 4 of Chance-Williams (or mitochondrial redox state 4, Chance B., Energy liked functions of mitochondria, New York, Acad. Press 1963)). The temperature of 27° C. corresponds to an oxygen concentration of approximately 250 µM. The metabolic state 3 of Chance-Williams is brought about by addition of 0.25 mM of adenosine diphosphate in control preparations containing 250 nM of riluzole.

The mean oxygen consumption of the control hepatic mitochondria is 1.63 µmol/min/mg of proteins (3 tests). In the presence of 250 nM of riluzole added in vitro to the mitochondria, the mean oxygen consumption is 2.12 µmol/min/mg of proteins (3 tests). These results show that riluzole stimulates mitochondrial respiration by about 30% relative to the controls.

Pharmaceutically acceptable salts which may be mentioned in particular are the addition salts with inorganic acids, such as hydrochloride, sulphate, nitrate or phosphate, or with organic acids, such as acetate, propionate, succinate, oxalate, benzoate, fumarate, maleate, methanesulphonate, isethionate, theophyllineacetate, salicylate, phenolphthalinate or methylenebis(β-hydroxynaphthoate), or substitution derivatives of these derivatives.

The medicinal products consist at least of riluzole, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally, parenterally, rectally or topically.

Solid compositions for oral administration which may be used are tablets, pills, powders (gelatin capsules, wafer capsules) or granules. In these compositions the active principle according to the invention is mixed with one or more inert diluents such as starch, cellulose, sucrose, lactose or silica, under a stream of argon. These compositions may also comprise substances other than diluents, for example one or more lubricants such as magnesium stearate or talc, a colouring, a coating (coated tablets) or a varnish.

Liquid compositions which may be used for oral administration are pharmaceutically acceptable solutions, suspensions, emulsions, syrups and elixirs, containing inert diluents such as water, ethanol, glycerol, vegetable oils or liquid paraffin. These compositions may comprise substances other than diluents, for example wetting, sweetening, thickening, flavouring or stabilizing products.

The sterile compositions for parenteral administration may preferably be solutions, aqueous or non-aqueous, suspensions or emulsions. As a solvent or vehicle, water, propylene glycol, polyethylene glycol, vegetable oils, especially olive oil, injectable organic esters, for example ethyl oleate, or other suitable organic solvents may be employed.

These compositions can also contain adjuvants, especially wetting, isotonizing, emulsifying, dispersing and stabilizing agents. Sterilization may be carried out in several ways, for example by aseptic filtration, by incorporation of sterilizing agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain both the active product and excipients such as cocoa butter, semisynthetic glycerides or polyethylene glycols.

The compositions for topical administration may for example be creams, lotions, mouth washes, nasal drops or aerosols.

The doses depend on the desired effect, on the duration of treatment and on the administration route used; they are generally between 50 and 400 mg per day by the oral route for an adult, with single doses ranging from 25 to 200 mg of active substance.

Generally speaking, the doctor will determine the appropriate dosage in accordance with the age, the weight and all of the other factors specific to the subject to be treated.

The examples which follow illustrate medicinal products according to the invention:

EXAMPLE A

The usual technique is used to prepare tablets containing a 50 mg dose of active product and having the following composition:

2-Amino-6-trifluoromethoxybenzothiazole 50 mg

Mannitol 64 mg

Microcrystalline cellulose 50 mg

Polyvidone excipient 12 mg

Sodium carboxymethylstarch 16 mg

Talc 4 mg

Magnesium stearate 2 mg

Anhydrous colloidal silica 2 mg

Mixture of methylhydroxypropylcellulose, polyethylene glycol 6000 and titanium dioxide (72:3.5:24.5)

q.s. 1 finished film-coated tablet weighing 245 mg

EXAMPLE B

The usual technique is used to prepare hard gelatin capsules containing a 50 mg dose of active product and having the following composition:

2-Amino-6-trifluoromethoxybenzothiazole 50 mg

Cellulose 18 mg

Lactose 55 mg

Colloidal silica 1 mg

Sodium carboxymethylstarch 10 mg

Talc 10 mg

Magnesium stearate 1 mg

EXAMPLE C

An injectable solution is prepared which contains 10 mg of active product and has the following composition:

2-Amino-6-trifluoromethoxybenzothiazole 10 mg

Benzoic acid 80 mg

Benzyl alcohol 0.06 cm3

Sodium benzoate 80 mg

Ethanol, 95% 0.4 cm3

Sodium hydroxide 24 mg

Propylene glycol 1.6 cm3

Water q.s. 4 cm3

The invention also relates to the process for the preparation of medicinal products which can be used in the treatment of mitochondrial diseases, consisting in mixing riluzole or the pharmaceutically acceptable salts of this compound with one or more compatible and pharmaceutically acceptable diluents and/or adjuvants.

We claim:

1. A method for the treatment of at least one mitochondrial disease, said method comprising administering to a patient in recognized need of said treatment an amount of riluzole or a pharmaceutically acceptable salt thereof effective for the treatment of said at least one mitochondrial disease.

2. The method of claim 1, wherein said mitochondrial disease is Kearns-Sayre syndrome, MERRF syndrome, MELAS syndrome or Leber's disease.

3. A method according to claim 1, wherein said riluzole or a pharmaceutically acceptable salt thereof is administered in an amount ranging from 50 to 400 mg per day.

4. A method according to claim 1, wherein said riluzole or a pharmaceutically acceptable salt thereof is administered in a dose ranging from 25 to 200 mg of active substance.

* * * * *